United States Patent
Kim et al.

(10) Patent No.: US 11,878,010 B2
(45) Date of Patent: Jan. 23, 2024

(54) COMPOSITION FOR PREVENTING OR TREATING CHRONIC OBSTRUCTIVE PULMONARY DISEASE COMPRISING REGORAFENIB AS ACTIVE INGREDIENT

(71) Applicant: Chungbuk National University Industry-Academic Cooperation Foundation, Chungcheongbuk-do (KR)

(72) Inventors: Eung Gook Kim, Chungcheongbuk-do (KR); Eun Young Shin, Chungcheongbuk-do (KR); Kwang Seok Oh, Chungcheongbuk-do (KR)

(73) Assignee: Chungbuk National University Industry-Academic Cooperation Foundation, Chungheongbuk-Do (KR)

( * ) Notice: Subject to any disclaimer, the term of this patent is extended or adjusted under 35 U.S.C. 154(b) by 0 days.

(21) Appl. No.: 17/811,050

(22) Filed: Jul. 6, 2022

(65) Prior Publication Data
US 2023/0061201 A1    Mar. 2, 2023

(30) Foreign Application Priority Data
Aug. 26, 2021    (KR) .......................... 10-2021-0113133

(51) Int. Cl.
*A61K 31/44* (2006.01)
*A61P 11/00* (2006.01)
*A61K 31/4412* (2006.01)
*A61P 35/00* (2006.01)

(52) U.S. Cl.
CPC .......... *A61K 31/4412* (2013.01); *A61P 35/00* (2018.01)

(58) Field of Classification Search
CPC ................................ A61K 31/44; A61P 11/00
See application file for complete search history.

(56) References Cited

U.S. PATENT DOCUMENTS

| | | |
|---|---|---|
| 10,272,252 B2 | 4/2019 | Iwase et al. |
| 2015/0297593 A1 | 10/2015 | Umetsu et al. |
| 2020/0206227 A1 | 7/2020 | Robinson et al. |
| 2021/0145740 A1 | 5/2021 | Hong et al. |

FOREIGN PATENT DOCUMENTS

| | | | |
|---|---|---|---|
| CN | 109820851 A | | 5/2019 |
| WO | WO 2016174183 | * | 11/2016 |

OTHER PUBLICATIONS

Korean Patent Application No. 10-2021-0113133, "Notification of Reason for Refusal," dated Oct. 11, 2021.
Korean Patent Application No. 10-2021-0113133, "Grant of Patent," dated Jan. 3, 2022.

* cited by examiner

*Primary Examiner* — Bruck Kifle
(74) *Attorney, Agent, or Firm* — Culhane Meadows PLLC; Robert C. Klinger

(57) ABSTRACT

Disclosed is a composition for preventing or treating chronic obstructive pulmonary disease containing regorafenib as an active ingredient, and particularly a pharmaceutical composition for preventing or treating chronic obstructive pulmonary disease containing regorafenib or a pharmaceutically acceptable salt thereof as an active ingredient, in which regorafenib is capable of effectively inhibiting increased immune response, which is a symptom of chronic obstructive pulmonary disease, and of improving and restoring changed lung structure and damaged lung function, and can be effectively used for the manufacture of a medicament for the prevention, amelioration, or treatment of chronic obstructive pulmonary disease, such as emphysema, chronic bronchitis, asthma, or pneumonia.

4 Claims, 4 Drawing Sheets

COMPOSITION FOR PREVENTING OR TREATING CHRONIC OBSTRUCTIVE PULMONARY DISEASE COMPRISING REGORAFENIB AS ACTIVE INGREDIENT

PRIORITY

This application claims the benefit of Korean Patent Application No. 10-2021-0113133, filed on Aug. 26, 2021, which application is hereby incorporated herein by reference.

TECHNICAL FIELD

The present invention relates to a composition for preventing or treating chronic obstructive pulmonary disease containing regorafenib as an active ingredient.

DESCRIPTION OF THE RELATED ART

Chronic obstructive pulmonary disease (COPD) is the number four cause of death worldwide as reported by the World Health Organization (WHO), and is a serious lung disease that is expected to rise to third place within 10 years. The major causes thereof are increased environmental pollution and increased exposure to various hazardous substances generated by industrial development, and in particular, COPD is an intractable chronic disease, which is mainly caused by smoking. Moreover, the incidence of COPD increases rapidly in the elderly population aged 65 years or older, and aging is also a major risk factor. However, since the diagnosis rate itself is very low and there is no clear therapeutic agent therefor, the mortality rate of COPD is increasing while the mortality rate of other serious chronic diseases is decreasing. Therefore, thorough research on the development of therapeutic agents capable of treating COPD is ongoing worldwide.

The typical clinical symptom of COPD is narrowing of the bronchiole, which makes breathing difficult. Because COPD progresses very slowly, many patients are not diagnosed or treated until the condition worsens, making it difficult to treat this disease. The major clinical diseases leading to COPD include emphysema and chronic bronchitis, and most chronic bronchitis patients who show symptoms of sputum production and coughing for a long time have a high probability of eventually being diagnosed with COPD. Moreover, in emphysema, the structure of the alveoli of the lungs is destroyed, preventing normal exchange of oxygen and carbon dioxide.

In particular, emphysema, one of the diseases belonging to COPD, causes damage to the alveoli or airways by exposing the lungs to toxic gases and substances emitted due to smoking or environmental pollution. The human body undergoes a repair process therefor, but this process is not properly controlled, causing abnormal and permanent damage to the lung structure, resulting in loss of lung function. In particular, the structure of the cells constituting the alveoli of the terminal bronchioles is destroyed, so the volume of space containing air is enlarged, and gas exchange does not occur properly. In addition, emphysema may be diagnosed through a bronchoalveolar lavage (BAL) fluid test for observing changes in the composition of immune cells due to an initial inflammatory response, a lung function test for measuring pulmonary respiration, and a morphological test for observing changes in the structure of the alveoli.

Meanwhile, materials currently used for the treatment of chronic obstructive pulmonary disease have been intensively developed to reduce inflammation in lung tissue, and steroids, anti-inflammatory drugs, and the like are mainly used therefor. However, these drugs cause various side effects such as tolerance and the like and are not suitable for patients with chronic obstructive pulmonary disease who require long-term treatment, and the therapeutic effect thereof is insufficient, which is undesirable.

Therefore, it is necessary to develop a new drug capable of effectively treating chronic obstructive pulmonary disease.

CITATION LIST

Patent Literature (Patent Document 1) U.S. patent Ser. No. 10/273,252

SUMMARY

Accordingly, the present inventors have screened about 1,000 FDA drugs for pharmacologically active drugs in order to develop a new drug capable of effectively treating chronic obstructive pulmonary disease, and ascertained that regorafenib, known as an anticancer drug, is very effective at treating chronic obstructive pulmonary disease, thus culminating in the present invention.

Accordingly, an object of the present invention is to provide a pharmaceutical composition for preventing or treating chronic obstructive pulmonary disease containing regorafenib or a pharmaceutically acceptable salt thereof as an active ingredient.

In order to accomplish the object of the present invention as described above, the present invention provides a pharmaceutical composition for preventing or treating chronic obstructive pulmonary disease containing regorafenib or a pharmaceutically acceptable salt thereof as an active ingredient.

In an embodiment of the present invention, regorafenib may have activities of inhibiting immune response, decreasing increased alveolar size, and improving lung function.

In an embodiment of the present invention, regorafenib may inhibit the immune response by inhibiting the proliferation of immune cells or the secretion of inflammatory mediators.

In an embodiment of the present invention, the immune cells may be macrophages, lymphocytes, eosinophils, or neutrophils.

In an embodiment of the present invention, the chronic obstructive pulmonary disease may be emphysema, chronic bronchitis, asthma, or pneumonia.

BRIEF DESCRIPTION OF THE DRAWINGS

The above and other objects, features, and other advantages of the present invention will be more clearly understood from the following detailed description taken in conjunction with the accompanying drawings, in which.

DETAILED DESCRIPTION OF ILLUSTRATIVE EMBODIMENTS

Figure 1A:
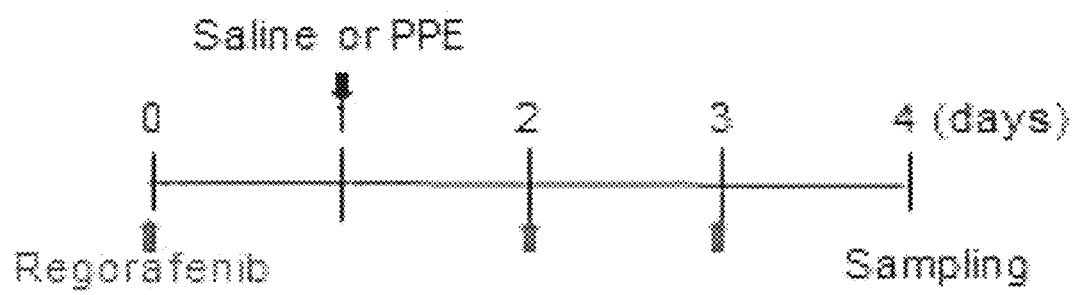
FIGS. 1A to 1D show results confirming the immune response inhibitory effect through treatment with regorafenib in a mouse animal model with emphysema induced by administration of porcine pancreatic elastase (PPE), FIG. 1A schematically showing the experimental schedule, FIG. 1B being images showing the results of staining immune cells in a control group, a PPE treatment group, and a PPE and regorafenib treatment group, and FIGS. 1C and 1D being graphs showing the number of immune cells and the number of cells depending on the type of immune cell.

The present invention discloses that it has been identified that regorafenib is capable of being used as a novel therapeutic agent for chronic obstructive pulmonary disease (COPD).

Regorafenib, an anticancer drug developed by Bayer, was approved by the US FDA on Sep. 27, 2012 after the effectiveness thereof in the treatment of advanced colorectal cancer was demonstrated, and since then its therapeutic use has been approved for various types of cancer, such as advanced gastrointestinal stromal tumors and advanced hepatocellular carcinoma.

Meanwhile, there has been no report yet that regorafenib is capable of preventing, ameliorating, or treating chronic obstructive pulmonary disease.

Accordingly, the present inventors have made great efforts to discover a novel therapeutic agent for chronic obstructive pulmonary disease (COPD), and ascertained effects of amelioration and treatment of chronic obstructive pulmonary disease including emphysema when administering regorafenib to mice with chronic obstructive pulmonary disease including emphysema.

Specifically, according to an embodiment of the present invention, regorafenib was administered to an animal model with chronic obstructive pulmonary disease induced by reducing elastin content using porcine pancreatic elastase (PPE), particularly to a mouse exhibiting the pathology of emphysema, after which whether the immune response was inhibited was analyzed.

In chronic obstructive pulmonary disease, an excessive immune response occurs in damaged lung tissue, and the activated immune response promotes the proliferation of immune cells and the secretion of various inflammatory mediators. Therefore, based on the results of evaluating whether the immune response was inhibited when mice with chronic obstructive pulmonary disease were treated with regorafenib, it has been confirmed that proliferation of immune cells, such as macrophages, lymphocytes, eosinophils, and neutrophils, was inhibited, and also that the secretion of inflammatory mediators was inhibited, thereby inhibiting the immune response.

Compared to normal persons, the number of macrophages is increased 5 to 10 times in the airways, lung parenchyma, and bronchoalveolar lavage fluid of patients with chronic obstructive pulmonary disease, and the number of macrophages is known to be correlated with the severity of disease. In chronic obstructive pulmonary disease, activated macrophages generate inflammatory mediators such as TNF-α (tumor necrosis factor-α), IL-8, CXC chemotactic substances, and the like, as well as oxygen groups, while simultaneously secreting proteolytic enzymes such as MMP-2, MMP-9, MMP-12, neutrophils, elastase, and the like, thus leading to damage to lung tissue.

For neutrophils, the number of activated neutrophils is increased in patients with chronic obstructive pulmonary disease, and neutrophils are able to secrete proteolytic enzymes such as elastase, cathepsin G, proteinase 3, MMP-8, and MMP-9, thereby contributing to lung tissue destruction.

It is also known that the number of eosinophils is increased in lung tissue in chronic obstructive pulmonary disease.

Moreover, smoking is considered the most important cause among the causes of chronic obstructive pulmonary disease, and smoke acts as a strongly toxic substance in the lung tissue, promoting the production of oxidizing substances, pro-inflammatory factors, and chemotactic factors, which promotes excessive migration of inflammatory cells such as neutrophils. Inflammatory cells migrated into the lung tissue also secrete many inflammatory mediators, further exacerbating inflammation of lung tissue. The most well-known mediators of the inflammatory response are TNF-α, MIP-1, CXCL-1, and the like.

In this regard, regorafenib according to the present invention is capable of inhibiting the proliferation of immune cells in damaged lung tissue, thereby suppressing the exacerbation of chronic obstructive pulmonary disease caused by excessive immune and inflammatory responses of immune cells.

In another embodiment of the present invention, the lung structure was analyzed in a mouse group with chronic obstructive pulmonary disease and a treatment group in which regorafenib is administered to the mouse with chronic obstructive pulmonary disease.

As a result, the alveolar size was found to increase in the mouse group with chronic obstructive pulmonary disease, whereas the increased alveolar size was decreased in the group administered with regorafenib. Therefore, based on these results, it was found that regorafenib is capable of regulating structural changes in the alveoli observed in chronic obstructive pulmonary disease.

In still another embodiment of the present invention, whether regorafenib is able to regulate lung function was evaluated. It has been confirmed that treatment with regorafenib in mice with chronic obstructive pulmonary disease inhibited the loss of lung function, compared to the regorafenib non-treated group.

Therefore, the present invention provides a pharmaceutical composition for preventing or treating chronic obstructive pulmonary disease containing regorafenib or a pharmaceutically acceptable salt thereof as an active ingredient.

Regorafenib of the present invention has all of activities of inhibiting immune response, reducing increased alveolar size, and improving lung function.

The chronic obstructive pulmonary disease capable of being prevented, ameliorated, or treated using the composition of the present invention may be selected from the group consisting of, but not limited to, emphysema, chronic bronchitis, asthma, and pneumonia.

Here, chronic obstructive pulmonary disease (COPD) is a disease in which an abnormal inflammatory response occurs in the lungs due to inhalation of harmful particles or gases, which gradually restricts airflow, thereby deteriorating lung function and causing dyspnea. The main symptoms of chronic obstructive pulmonary disease include chronic coughing or chronic sputum (phlegm) production and shortness of breath. Bronchodilators such as beta agonists, anticholinergics, methylxanthine, and the like or adrenocortical hormone inhalants are used as representative therapeutic agents.

Also, chronic bronchitis is exhibited as persistent coughing and sputum production for 3 months or more per year for 2 consecutive years, and is presumed to be caused by bronchial damage due to stimuli such as smoking, air pollution, occupational exposure, and the like. Other major symptoms include chronic coughing, sputum production, shortness of breath during exercise, and the like. In addition, acute exacerbation of chronic obstructive pulmonary disease may occur, in which case shortness of breath rapidly worsens over several hours to several days, and the amount of sputum increases or the sputum changes from mucoid to purulent, so it takes on a dark yellow or bluish color and increases in viscosity, making it difficult to spit out.

Also, emphysema is abnormal and permanent dilatation of the peripheral airways and alveoli due to destruction of airspace distal to the terminal bronchioles. It is caused by inhalation of harmful particles and gases, and the most clinically significant risk factor is known to be smoking. The main symptoms thereof include chronic coughing, sputum production, shortness of breath, and the like.

The pharmaceutical composition according to the present invention may contain a pharmaceutically acceptable carrier, in addition to the active ingredient. Such a carrier may be of a type that is commonly used in formulations, and examples thereof include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, and mineral oil. The pharmaceutical composition of the present invention may further contain a lubricant, a wetting agent, a sweetener, a flavoring agent, an emulsifier, a suspension agent, a preservative, and the like, in addition to the above components. Suitable pharmaceutically acceptable carriers and formulations are described in detail in Remington's Pharmaceutical Sciences (19th ed., 1995).

A suitable dosage of the pharmaceutical composition according to the present invention may vary depending on factors such as the formulation method, administration mode, patient's age, body weight, gender, and pathological status, food, administration time, administration route, excretion rate, and response sensitivity. The dosage of the pharmaceutical composition of the present invention is preferably 0.0001-100 mg/kg (body weight) per day.

The pharmaceutical composition of the present invention may be administered orally or parenterally, and for parenteral administration, topical application to the skin, intravenous injection, subcutaneous injection, intramuscular injection, intraperitoneal injection, transdermal administration, and the like may be carried out. The concentration of the active ingredient contained in the composition of the present invention may be determined in consideration of the therapeutic purpose, the patient's condition, the required period, etc., and is not limited to a concentration within a specific range.

The pharmaceutical composition of the present invention is formulated in a unit dosage form or into a multi-dose container using a pharmaceutically acceptable carrier and/or excipient according to a method that may be easily carried out by a person of ordinary skill in the art to which the present invention belongs. Here, the formulation may be provided in the form of a solution, suspension, or emulsion in an oily or aqueous medium, or may take a form such as an extract, powder, granule, tablet, or capsule, and may further include a dispersant or stabilizer.

As used herein, the term "treatment" refers to any action that reverses or alleviates a disease or disorder to which the term is applied, or one or more symptoms of the disease or disorder, or inhibits or prevents the progression thereof, unless otherwise stated.

A better understanding of the present invention may be obtained through the following examples. These examples are set forth to illustrate the present invention, but are not to be construed as limiting the scope of the present invention.

PREPARATION EXAMPLE

Preparation of Materials and Reagents

PPE (EC134: elastase from porcine pancreas) was purchased from EPC and used, and regorafenib was obtained from SelleckChem. HBSS (Hanks' balanced salt solution) and red blood cell lysis buffer were purchased from Sigma Aldrich and used. A NovaUltr™ Hema-Diff Stain Kit was purchased from IHCWORLD. Lung function was measured using a flexiVent system available from SCUREQ. All experimental animals were used for experimentation according to animal protocols and guidelines set forth by the Institutional Animal Care and Use Committee (CBNUA-1470-20-01) of Chungbuk National University, Korea. C57BL/6 mice (6 to 8 weeks old) used in experiments were purchased from Daehan Biolink.

Example 1

Analysis of Immune Response Inhibitory Effect Through Treatment with Regorafenib in Animal Model with Chronic Obstructive Pulmonary Disease The present inventors performed an experiment to determine whether regorafenib has activity capable of treating chronic obstructive pulmonary disease. The initial response induced by PPE (porcine pancreatic elastase) representatively includes immune responses that occur in damaged lung tissue. The activated immune response promotes the proliferation of various immune cells and the secretion of various inflammatory mediators. Specifically, the overall number of immune cells increases with an increase in individual immune cells involved in the immune response. In particular, an increase in the numbers of macrophages, lymphocytes, eosinophils, and neutrophils is observed. The increase in the number of these cells can be confirmed through a bronchoalveolar lavage (BAL) fluid test.

Therefore, in the present invention, mice with chronic obstructive pulmonary disease, particularly emphysema, in which alveolar damage was induced by reducing elastin content using PPE, were prepared and then treated with regorafenib to thus analyze whether chronic obstructive pulmonary disease was ameliorated. Specifically, 6-week-old C57BL/6 mice were purchased and acclimatized for one week. Thereafter, the acclimatized 7-week-old mice (average 25 g) were orally administered with 200 µl of regorafenib (SelleckChem, BAY 73-4506) at a concentration of 5 mg/kg. The next day, that is, on day 1, each mouse's status was observed, followed by nasal administration of PPE [elastase from porcine pancreas] (EPC, EC134) at a concentration of 5 U. Then, each mouse's status was observed on days 2 and 3, followed by oral administration of 200 µl of regorafenib at a concentration of 5 mg/kg. On day 4, the mice were anesthetized using 200 µl of anesthetic (Zoletil to rompun to saline at a ratio of 1:1:8), after which the neck of each mouse was incised to thus expose the airway, which was then cut in half and a catheter was inserted therein. Thereafter, 1 ml of HBSS [Hanks' balanced salt solution] (Sigma Aldrich, H6648) was placed in a syringe, which was then connected to the catheter, after which procedures of injection and then extraction were performed three times to collect the BAL fluid. The BAL fluid thus obtained was centrifuged to collect cells, and the collected cells were suspended in HBSS, treated with a red blood cell lysis buffer (Sigma Aldrich, 11814389001) at 1:1, allowed to react at room temperature for 2 minutes, further added with HBSS, and then centrifuged. In this procedure, red blood cells are removed. The centrifuged cells were diluted and centrifuged using a Cytospin (Hanil Science), and then attached to a slide. The attached cells were stained using a NovaUltr™ Hema-Diff Stain Kit (IHCWORLD, IW-3017) according to the manufacturer's instructions. The stained slide was analyzed and quantified using a microscope.

According to the method described above, a mouse animal model of chronic obstructive pulmonary disease was prepared by administering the mouse lungs with 5 U of PPE, and in order to verify whether the immune response was modulated, one day before administration of PPE and on days 2 and 3 after administration of PPE, regorafenib (5 mg/kg) was administered thereto, and on day 4, bronchoalveolar lavage fluid was obtained and the immune cells therein were stained to thus quantitatively analyze the type of immune cells and the number of individual cells. Here, mice administered only with saline were used as a control group, and 5 mice were placed in each group.

Figure 1B:
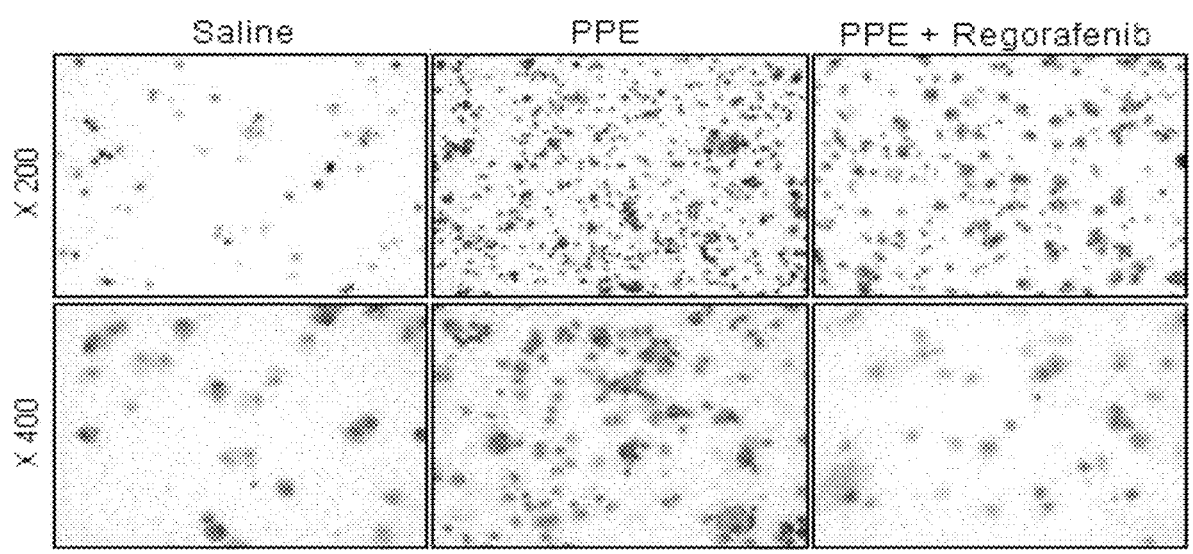
Figure 1C:
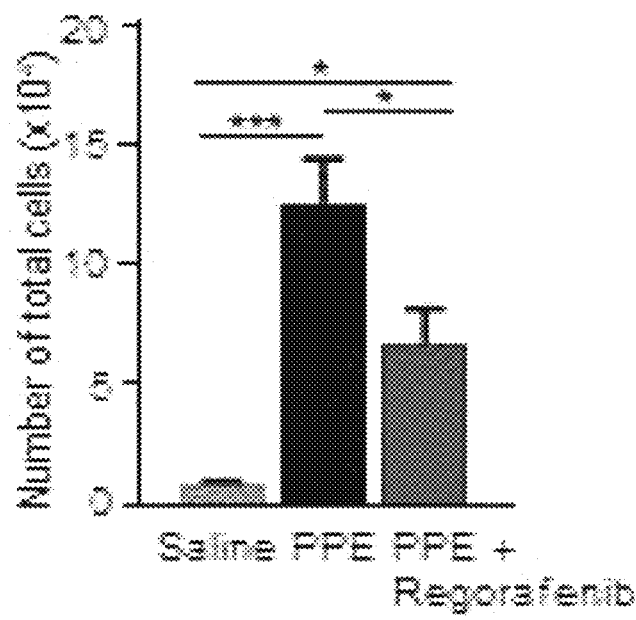
Figure 1D:
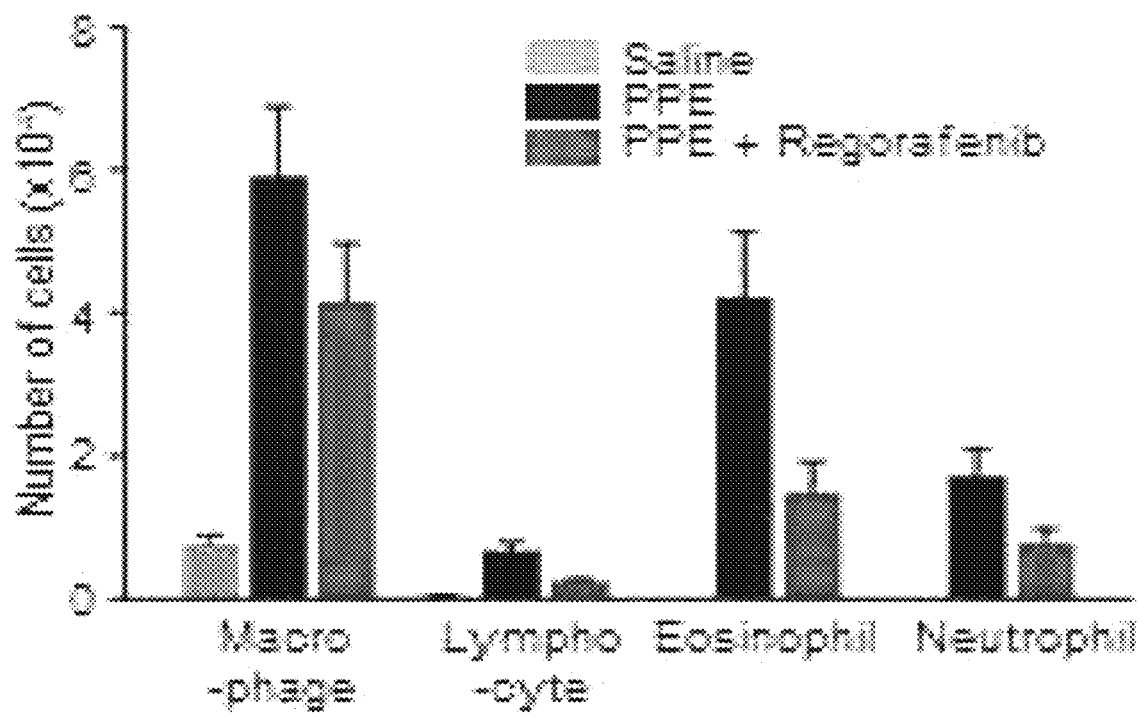

Based on the results of analysis, the number of immune cells increased significantly in the PPE treatment group compared to the control group, whereas in the regorafenib treatment group, the number of immune cells increased due to PPE decreased by about 50% (FIGS. 1B and 1C). Among the types of immune cells that increased in number, the number of macrophages was found to have increased the most, and the number of macrophages was decreased from about $6 \times 10^4$ to $4 \times 10^4$ through treatment with regorafenib (FIG. 1D). In addition, it was confirmed that the number of lymphocytes was increased to $6 \times 10^3$ but was decreased to about $2.5 \times 10^3$ by regorafenib. In addition, it was confirmed that the numbers of eosinophils and neutrophils were significantly decreased through treatment with regorafenib.

Based on these results, the present inventors have found that regorafenib of the present invention is capable of inhibiting or reducing the increase in the initial immune response, which is a symptom of chronic obstructive pulmonary disease.

Example 2

Analysis of Improvement Effect of Changes in Lung Structure Through Treatment with Regorafenib in Animal Model with Chronic Obstructive Pulmonary Disease One of the pathological indicators of chronic obstructive pulmonary disease is changed alveolar size. Changes in the alveolar size can be analyzed by quantifying the mean linear intercept (Lm) value, representing the average distance between the alveolar walls, in a microscopic field of view. When chronic obstructive pulmonary disease is induced, this value increases, indicating an increase in the alveolar size.

Figure 2A:
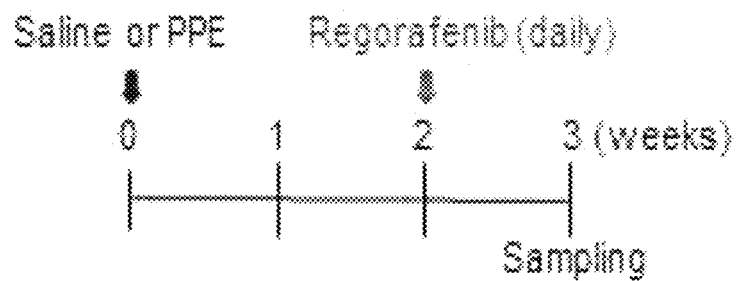
FIGS. 2A to 2C show results confirming lung structure changes through treatment with regorafenib in a mouse animal model with emphysema induced by administration of PPE, FIG. 2A schematically showing the experimental schedule, FIG. 2B being images showing structural changes in the alveoli through H&E staining in a control group, a PPE treatment group, and a PPE and regorafenib treatment group, and FIG. 2C showing the results of analysis of the measured value Lm, which is the average distance between the alveolar walls.

Therefore, the present inventors analyzed whether it is possible to alleviate changes in lung structure by measuring the change in Lm value due to treatment with regorafenib in a mouse animal model with emphysema, a chronic obstructive pulmonary disease, prepared over three weeks through administration of PPE (FIG. 2A).

Specifically, 6-week-old C57BL/6 mice were acclimatized for one week, after which the acclimatized 7-week-old mice (average 25 g) were subjected to nasal administration with saline and PPE [elastase from porcine pancreas] (EPC, EC134) at a concentration of 5 U. Two weeks after administration, the mice were orally administered with 200 μl of regorafenib (SelleckChem, BAY 73-4506) at a concentration of 5 mg/kg for one week, and on week 3, the lungs were extracted from each mouse, placed in a cassette, immersed in 10% NBF, and stored for one day, after which a parafilm block was prepared using a tissue processor. The prepared block was cut using a sectioning machine, attached to a slide, subjected to H&E staining, and then quantified by measuring the Lm value based on microscopic images.

Figure 2B:
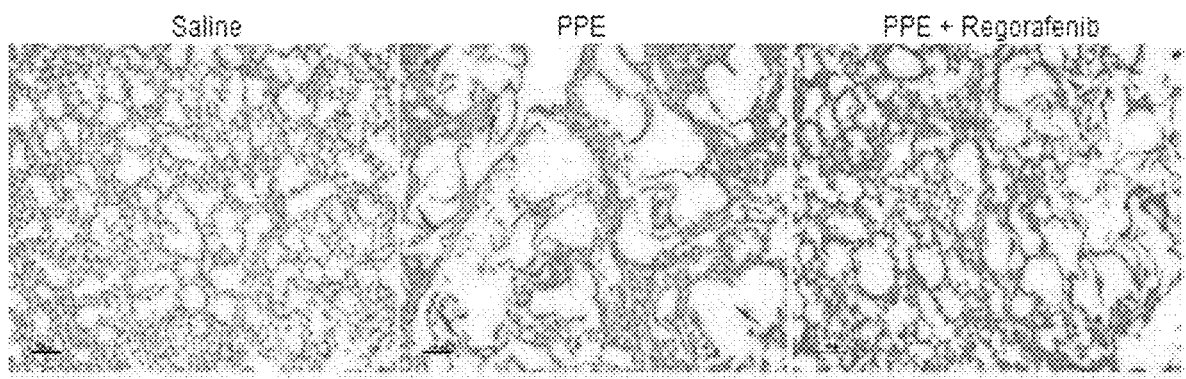
Figure 2C:
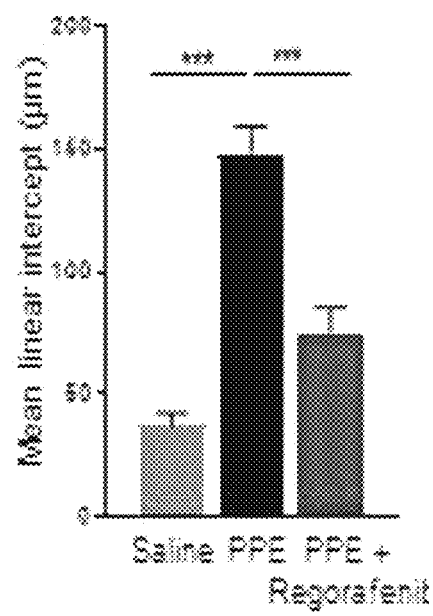

Based on the results of analysis, as shown in FIGS. 2B and 2C, the Lm value significantly increased in the PPE treatment group compared to the control group, whereas in the regorafenib treatment group, the Lm value decreased by about 50% compared to the PPE treatment group. Through these results, the present inventors confirmed that chronic obstructive pulmonary disease was normally induced in mice due to PPE administration in this experiment, and also that the changed lung structure in the induced chronic obstructive pulmonary disease was reversed and restored so as to be comparable to the normal state by regorafenib.

Therefore, it has been found that regorafenib has activity capable of improving and regulating structural changes in alveoli accompanying chronic obstructive pulmonary disease.

Example 3

Analysis of Lung Function Regulatory Effect of Regorafenib in Animal Model with Chronic Obstructive Pulmonary Disease In addition, the present inventors performed an experiment to determine whether regorafenib is able to restore lost function of damaged lungs in order to confirm whether regorafenib is able to treat chronic obstructive pulmonary disease.

Specifically, 6-week-old C57BL/6 mice were purchased and acclimatized for one week, after which the acclimatized 7-week-old mice (average 25 g) were subjected to nasal administration with saline and PPE [elastase from porcine pancreas] (EPC, EC134) at a concentration of 5 U. Two weeks after administration, the mice were orally administered with 200 μl of regorafenib (SelleckChem, BAY 73-4506) at a concentration of 5 mg/kg for one week. Then, the mice were anesthetized using 300 μl of anesthetic on week 3, after which the lung function of each mouse was measured using a flexiVent (system for measuring the function of lungs) and quantified by subtracting the error value therefrom.

Figure 3:
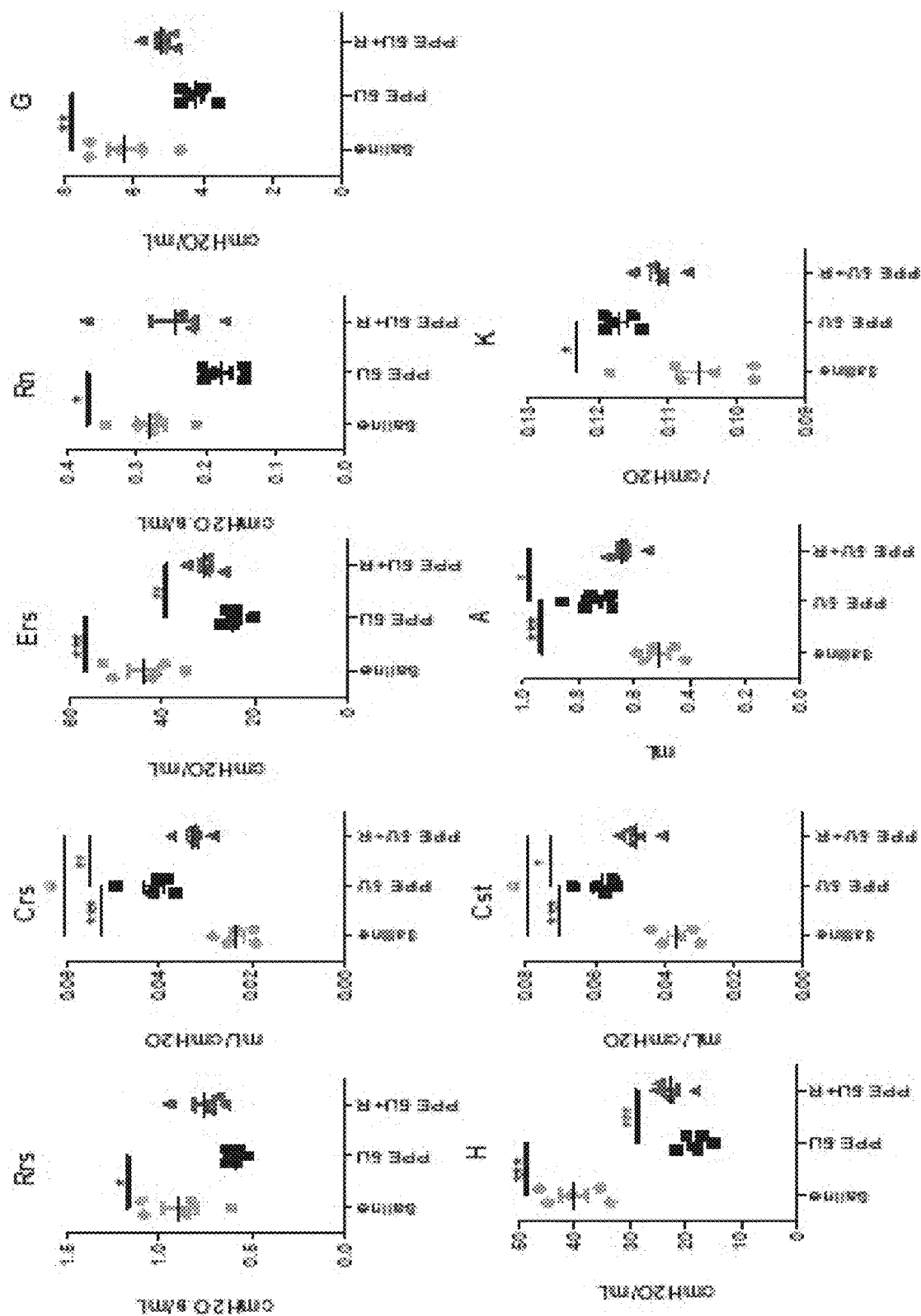
FIG. 3 shows the results of measuring changes in various lung function indicators, which are results of analyzing the changes in the lung function through treatment with regorafenib in a mouse animal model with emphysema induced by administration of PPE.

As shown in FIG. 3, it could be confirmed that various lung function indicators lost in mice with chronic obstructive pulmonary disease induced by PPE administration were restored through treatment with regorafenib.

Based on the aforementioned results, the present inventors confirmed that regorafenib is capable of inhibiting increased immune response caused by chronic obstructive pulmonary disease, and of improving and restoring damaged and changed lung structure and lung function, whereby regorafenib can be used as a novel therapeutic agent for chronic obstructive pulmonary diseases including emphysema, chronic bronchitis, asthma, and pneumonia.

As is apparent from the above description, regorafenib according to the present invention is capable of inhibiting increased immune response, which is a symptom of chronic obstructive pulmonary disease, and of improving and restoring changed lung structure and damaged lung function, and can be effectively used for the manufacture of a medicament for the prevention, amelioration, or treatment of chronic obstructive pulmonary disease.

Although preferable exemplary embodiments of the present invention have been disclosed in detail above, it will be obvious to those skilled in the art that the present invention may be implemented in a modified form without departing from the essential characteristics of the present invention. Therefore, the disclosed embodiments are to be considered in an illustrative rather than a restrictive way. The scope of the present invention is indicated in the claims rather than the foregoing description, and all differences within the scope equivalent thereto should be construed as being included in the present invention.

What is claimed is:

1. A method for treating emphysema, administering to subject in need thereof a pharmaceutical composition comprising regorafenib or a pharmaceutically acceptable salt thereof as an active ingredient.

2. The method of claim 1, wherein the regorafenib has activities of inhibiting an immune response, decreasing an increased alveolar size, and improving a lung function.

3. The method of claim 2, wherein the regorafenib inhibits the immune response by inhibiting proliferation of immune cells or secretion of inflammatory mediators.

4. The method of claim 3, wherein the immune cells are macrophages, lymphocytes, eosinophils, or neutrophils.

* * * * *